US00PP34216P2

(12) United States Plant Patent
Growns

(10) Patent No.: US PP34,216 P2
(45) Date of Patent: May 10, 2022

(54) ***GREVILLEA* PLANT NAMED 'ETERNAL BLAZE'**

(50) Latin Name: ***Grevillea* hybrid *(Grevillea nivea* x *Grevillea variifolia)***
Varietal Denomination: Eternal Blaze

(71) Applicant: Botanic Gardens and Parks Authority, Perth (AU)

(72) Inventor: Digby James Growns, Perth (AU)

(73) Assignee: BOTANIC GARDENS AND PARKS AUTHORITY, Perth (AU)

( * ) Notice: Subject to any disclaimer, the term of this patent is extended or adjusted under 35 U.S.C. 154(b) by 0 days.

(21) Appl. No.: 17/136,091

(22) Filed: Dec. 29, 2020

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00
See application file for complete search history.

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of *Grevillea* Plant, referred to by its cultivar name, 'Eternal Blaze', is disclosed. The new variety forms attractive, red colored flowers. Silver colored foliage is formed. The vegetation is moderately vigorous, and the growth habit is prostrate and groundcover-like. The new variety is particularly well suited for providing distinctive ornamentation in the landscape.

1 Drawing Sheet

Botanical/commercial classification:
Latin name: *Grevillea* hybrid (*Grevillea nivea* x *Grevillea variifolia*).
Varietal denomination: 'Eternal Blaze'.

SUMMARY OF THE INVENTION

The new variety of *Grevillea* plant, botanically known as *Grevillea* hybrid and also known as *Grevillea nivea* x *Grevillea variifolia*, of the present invention originated by cross pollination in Perth, Western Australia, wherein two parents were crossed which previously had been studied in the hope that they would contribute the desired characteristics. The female parent (i.e., the seed parent) was the *Grevillea nivea* '20091434' variety (not patented). The male parent (i.e., the pollen parent) was the *Grevillea variifolia* '19920690' variety (not patented).

The parentage can be summarized as follows:

'20091434' x '19920690'

The new cultivar was discovered and selected as a single flowering plant within the progeny of the above stated cross pollination during November 2011 in a controlled environment in Perth, Western Australia.

It was found that the new variety of *Grevillea* plant of the present invention possesses the following combination of characteristics:

(a) forms red colored flowers,
(b) exhibits silver colored foliage,
(c) provides moderately vigorous vegetation, and
(d) forms prostrate and groundcover-like growth habit.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the '20091434' variety (i.e., the seed parent) displays less silver colored foliage compared to the new variety. The '19920690' variety (i.e., the pollen parent) displays a less prostrate growth habit compared to the new variety. Moreover, the new variety can be readily distinguished from other similar non-parental varieties. For example, the 'Poorinda Royal Mantel' variety (non-patented) exhibits weaker red flower color compared to the new variety.

The new variety has been found to undergo asexual propagation in Perth, Western Australia by stem cuttings since November 2011. Asexual propagation by stem cuttings in Perth, Western Australia has shown that the characteristics of the new variety are homogeneous, stable, and strictly transmissible by such asexual propagation from one generation to another. Accordingly, the new variety undergoes asexual propagation in a true-to-type manner.

The new variety has been named 'Eternal Blaze'.

BRIEF DESCRIPTION OF THE PHOTOGRAPH

The accompanying photograph shows, as nearly true as it is reasonably possible to make the same in color illustrations of this character, a typical specimen of the new variety. Colors in the photograph differ slightly from the color designations cited in the detailed description, which accurately describes the colors of the new variety. The plant was grown in a three-gallon container for two years in an outdoor nursery in Arroyo Grande, Calif.

Drawing—illustrates a specimen of the plant displaying the overall growth and flowering habit—side view.

DETAILED BOTANICAL DESCRIPTION

The chart used in the identification of colors described herein is that of The Royal Horticultural Society (R.H.S. Colour Chart) London, England, 2001 edition, except where general color terms of ordinary significance are used. The terminology which precedes reference to the chart has been added to indicate the corresponding color in more common terms. The following measurements and numerical values represent averages of typical plants.

Propagation:

*Type cutting*.—Terminal stem cuttings.

*Time to initiate roots*.—Approximately 14 to 18 weeks.

*Time to produce a rooted cutting*.—Approximately 24 to 28 weeks.

*Root description*.—Light brown in color, fine.

*Rooting habit*.—Freely branching.

Plant:

*Growth habit and general appearance*.—Full, moderately vigorous, prostrate and groundcover like growth habit with foliage that appears silver in full sun.

*Size*.—Height: approximately 0.5 m after five years of age. Width: approximately 2.0 to 3.0 m after five years of age.

*Branching habit*.—Freely branching. Quantity of branches per plant: approximately 8. Branch Strength: strong. Lateral branch shape: cross-section is angular. Length to base of peduncle: approximately 12.0 to 16.0 cm. Diameter: approximately 1.5 to 2.5 cm. Length of central internode: approximately 4.0 to 6.0 cm. Texture: barely pubescent. Stem shape: cross-section is round and slightly ribbed. Pubescence color: commonly near White Group 155C. Color of young stems: commonly near Yellow-Green Group 145C. Color of mature stems: commonly near Yellow-Green Group N144D.

Foliage:

*General description*.—Fragrance: none detected. Density: moderate, significantly more dense on mature growth.

*Leaf*.—Form: simple. Arrangement: alternate. Aspect: acute angle to stem. Margin: lobed. Undulation of margin: weak. Apex: acute (lobes). Base: narrow attenuate. Profile of leaf cross-section: appressed. Venation pattern: pinnate. Venation color: upper and lower sides are commonly near Yellow-Green Group 144A. Length of mature leaf: approximately 27.0 to 29.0 cm. Width of mature leaf: approximately 28.0 to 30.0 cm. Texture of upper surface: slightly pubescent. Texture of lower surface: barely pubescent. Pubescence color: commonly near White Group 155C. Color of upper surface of young foliage: commonly near Green Group 143C. Color of lower surface of young foliage: commonly near Greyed-Green Group 192C. Color of upper surface of mature foliage: commonly near Green Group N138B. Color of lower surface of mature foliage: commonly near Greyed-Green Group 192C.

*Petiole*.—Length: approximately 5 to 10 mm. Width: approximately 2 to 3 mm. Texture: pubescent. Color: commonly near Greyed-Green Group 192B.

*Stipule*.—Arrangement: intrapetiolar. Texture: pubescent. Shape: spinose. Length: approximately 5 to 15 mm. Width: approximately 2 to 3 mm. Color: commonly near Greyed-Green Group 192D.

Flower:

*Flowering habit*.—Freely flowering.

*Lastingness of individual inflorescence on the plant/flower persistence*.—Approximately 10 to 14 days.

Inflorescence description:

*General description*.—Type: raceme. Shape: secund conflorescence, florets primarily facing one side. Aspect: facing upward and outward. Arrangement: terminal and from leaf axils. Fragrance: none detected. Quantity per plant: approximately 8. Flower diameter: approximately 2.5 cm. Flower depth: approximately 7.0 cm. Attitude of tepal limb in relation to the longitudinal axis of the flower bud: upright.

*Bud*.—Rate of opening: approximately 3 to 4 days. Shape: spike. Diameter: approximately 3.0 mm. Texture of outer surface: pubescent. Pubescence color: commonly near White Group 155C. Color: commonly near Green Group 129C.

*Florets*.—Quantity per inflorescence: approximately 70. Arrangement: in pairs. Length: approximately 3.0 cm. Diameter: approximately 0.7 mm.

*Perianth*.—Shape: tubular with a ventral limb that becomes revolute during anthesis. Length: approximately 2.0 cm. Diameter at widest point: approximately 1.0 cm. Diameter as base: approximately 4.0 to 5.0 mm. Perianth coherence of tepals on the dorsal side: one third to two thirds.

*Tepals*.—Quantity: 4. Shape: linear. Margin: entire. Apex: angle. Length: approximately 2.0 cm. Width: approximately 1.0 cm. Texture of outer surface: pubescent. Texture of inner surface: smooth. Color of outer surface when fully open: commonly near Greyed-Green Group 196C. Color of inner surface when fully open: commonly near Greyed-Green Group 192B.

*Peduncle*.—Strength: strong. Aspect: erect. Length: approximately 1.0 to 1.5 cm. Diameter: approximately 4.0 mm. Texture: pubescent. Color: commonly near Yellow-Green Group 145C.

*Rachis*.—Strength: strong, erect. Length: approximately 5.0 to 6.0 cm. Diameter: approximately 4.0 mm. Texture of outer surface: pubescent. Pubescence color: commonly near Green-White Group 157A.

*Pedicel*.—Strength: strong. Aspect: upright. Length: approximately 1.0 to 2.0 mm. Diameter: approximately 0.9 mm. Texture of outer surface: slightly pubescent. Pubescence color: commonly near Green-White Group 157A. Color: commonly near Yellow-Green Group 145C.

*Reproductive organs*.—Anther quantity: 2 per floret. Anther Shape: bilobed. Anther length: approximately 2.0 to 5.0 mm. Anther color: commonly near Greyed-Orange Group 176B. Pollen amount: sparse. Pollen color: commonly near Greyed-Orange Group 163A. Pistil quantity: 1 per floret. Pistil length: approximately 17.0 mm and is twice the length of the perianth. Stigma shape: round. Stigma length: approximately 1.0 mm. Stigma color: commonly near Yellow-Orange Group 20C. Style length: approximately 5.0 cm. Style color: commonly near Red Group 45B. Style curvature: opens reflexed becoming slightly curved. Style hairiness: microscopically pubescent and distribution of style hair is evenly distributed along the length. Attitude of pollen presenter to style: oblique. Ovary length: approximately 0.5 mm. Ovary texture: pubescent. Ovary pubescence color: commonly near White Group 155B. Ovary color: commonly near Yellow-Orange Group 16C. Nectary length: approximately 0.5 to 1.0 mm. Nectary width: approximately 1.0 mm. Nectary color: commonly near Green-White Group 157D.

*Seed*.—Not observed to date.

Development:

*Disease and pest resistance*.—Resistance to pathogens and pests common to *Grevillea* has not been observed.

*Commercial crop time*.—Approximately 16-18 months for an 11 liter (3 gallon) container.

*Hardiness*.—USDA Zone 8 through 11.

Plants of the 'Eternal Blaze' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Grevillea* plant named 'Eternal Blaze' characterized by the following combination of characteristics:

(a) forms red colored flowers, (b) exhibits silver colored foliage, (c) provides moderately vigorous vegetation, and (d) forms prostrate and groundcover-like growth habit; substantially as herein shown and described.

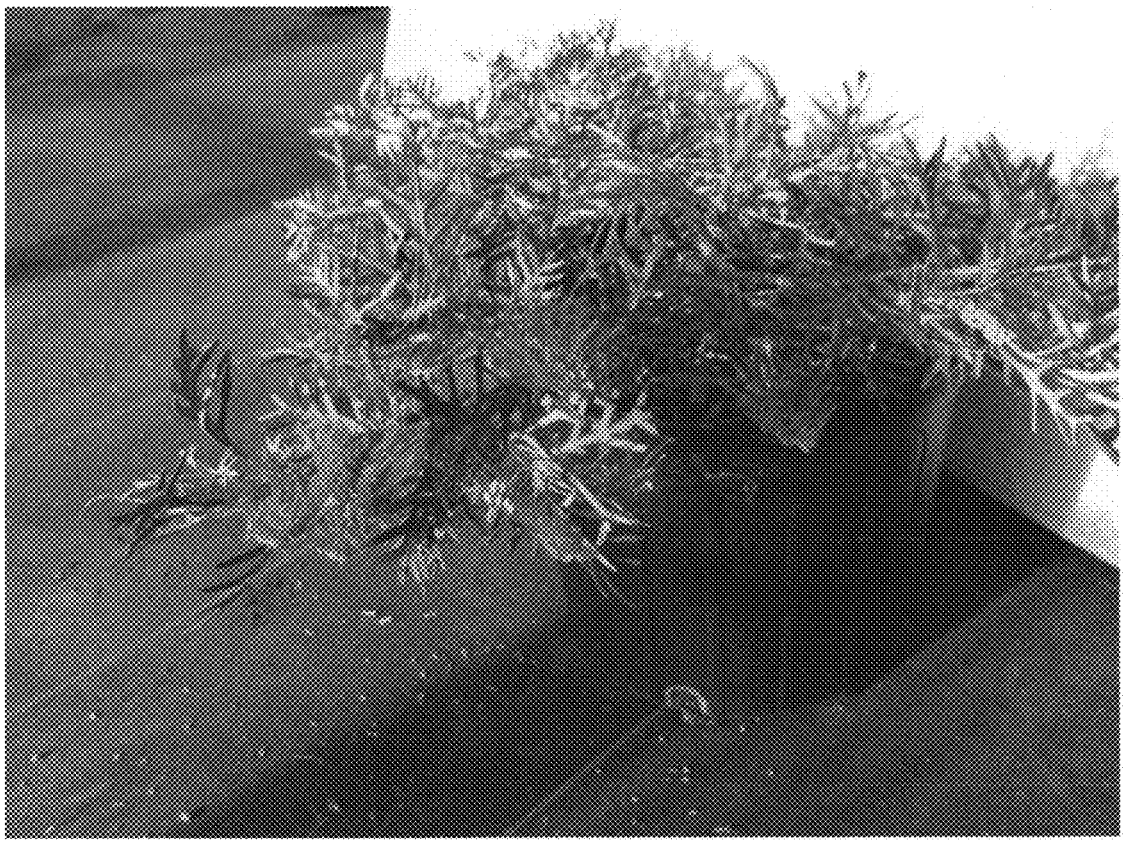

* * * * *